US008142358B2

(12) United States Patent
Pedrizzetti et al.

(10) Patent No.: US 8,142,358 B2
(45) Date of Patent: Mar. 27, 2012

(54) MEASUREMENT METHOD OF TIME VARYING EVENTS IN A TARGET BODY AND A METHOD FOR DISPLAYING MEASUREMENT DATA OF DIFFERENT PARAMETERS OF A TARGET IN WHICH TIME DEPENDENT EVENTS OCCUR

(75) Inventors: Gianni Pedrizzetti, Prato (IT); Marchese Emidio, Popoli (IT); Tonti Giovanni, Sulmona (IT)

(73) Assignee: Esaote S.p.A., Milan (IT)

( * ) Notice: Subject to any disclaimer, the term of this patent is extended or adjusted under 35 U.S.C. 154(b) by 1073 days.

(21) Appl. No.: 11/448,532

(22) Filed: Jun. 7, 2006

(65) Prior Publication Data

US 2006/0281993 A1 Dec. 14, 2006

(30) Foreign Application Priority Data

Jun. 8, 2005 (EP) .................................... 05425411

(51) Int. Cl.
*A61B 8/00* (2006.01)
(52) U.S. Cl. ........ 600/450; 600/438; 600/443; 600/437; 600/449; 382/128; 715/700
(58) Field of Classification Search .................. 600/437, 600/438, 443, 449, 450; 382/128; 715/700
See application file for complete search history.

(56) References Cited

U.S. PATENT DOCUMENTS 5,097,836 A 3/1992 Yamada et al. .......... 128/660.07
(Continued)

FOREIGN PATENT DOCUMENTS

EP 0 383 288 A1 8/1990
(Continued)

OTHER PUBLICATIONS

Urheim, et al., "Myocardial Strain by Doppler Echocardiography, Validation of a New Method to Quantify Regional Myocardial Function", *Circulation*, 2000; 102:1158-1164.

(Continued)

*Primary Examiner* — Brian Casler
*Assistant Examiner* — Amanda Lauritzen
(74) *Attorney, Agent, or Firm* — Woodard Emhardt Moriarty McNett & Henry

(57) ABSTRACT

A measurement method of time varying events in a target body, including the steps of (a) providing time dependent measurements signals of parameters of the time varying events in the target body, (b) providing ecographic M-mode image data whose spatial direction is along scan-lines or along a line or curve on a 2D or 3D image of an image sequence, (c) defining a time interval within which the measurement signal has to be displayed and/or evaluated, (d) generating bi-dimensional graph information, (e) generating bi-dimensional M-mode images, (f) determining the time instant of begin of the time interval having a univoquely relation to time varying events, (g) rescaling the time scale of each graph, and (h) displaying the graph of the function corresponding to one or more of the time dependent measurement signal on a background.

24 Claims, 5 Drawing Sheets

U.S. PATENT DOCUMENTS

| | | | |
|---|---|---|---|
| 5,515,856 A | 5/1996 | Olstad et al. | 128/661.04 |
| 5,653,237 A * | 8/1997 | Uchida | 600/456 |
| 5,820,561 A | 10/1998 | Olstad et al. | 600/453 |
| 6,174,287 B1 | 1/2001 | Resnick et al. | 600/458 |
| RE37,088 E | 3/2001 | Olstad et al. | 600/400 |
| 6,352,507 B1 | 3/2002 | Torp et al. | 600/438 |
| 6,537,221 B2 * | 3/2003 | Criton et al. | 600/454 |
| 6,589,175 B2 | 7/2003 | Prater et al. | 600/443 |
| 6,884,216 B2 * | 4/2005 | Abe et al. | 600/440 |
| 7,422,561 B2 * | 9/2008 | Kanai et al. | 600/437 |
| 2004/0111028 A1 | 6/2004 | Abe et al. | 600/437 |
| 2005/0124881 A1 | 6/2005 | Kanai et al. | 600/437 |
| 2007/0071295 A1 * | 3/2007 | Jackson | 382/128 |

FOREIGN PATENT DOCUMENTS

| | | |
|---|---|---|
| EP | 1 520 517 A1 | 4/2005 |
| EP | 1 522 875 A1 | 4/2005 |
| WO | WO 03/071950 A1 | 9/2003 |
| WO | WO 03/077765 A1 | 9/2003 |

OTHER PUBLICATIONS

D'hooge, et al., "Review Article, Regional Strain and Strain Rate Measurements by Cardiac Ultrasound: Principles, Implementation and Limitations", *Eur J. Echocardiography*, 2000; 1, 154-170.

* cited by examiner

MEASUREMENT METHOD OF TIME VARYING EVENTS IN A TARGET BODY AND A METHOD FOR DISPLAYING MEASUREMENT DATA OF DIFFERENT PARAMETERS OF A TARGET IN WHICH TIME DEPENDENT EVENTS OCCUR

CROSS-REFERENCES TO RELATED APPLICATIONS

The present application claims priority to EP 05425411.5, filed Jun. 8, 2005, and this reference is expressly incorporated by reference herein, in its entirety.

BACKGROUND OF THE INVENTION

The invention relates to a measurement method of time varying events in a target body.

Particularly the invention relates to a measurement method in which time dependent events are measured by means of several probes or devices capable of detecting and monitoring different parameters and among which also an ecographic imaging method is used.

Time varying events are often connected to motion or change in shape of a target body or parts thereof and these events can be measured or detected by means of ecographic, i.e. ultrasound imaging methods and devices.

M-mode ecographic images are useful instruments for measuring, monitoring or detecting the dynamic of biological targets and of unanimated targets as for example it is well known in echocardiology and in the assessment of industrial valvular dynamics to flying or deformable objects.

The so-called M-mode (Motion-mode) images, a name mostly used in echocardiography, is a two-dimensional image representation where one axis, normally the abscissa, is the time direction, and one axis is one space line or curve within a higher dimensional space along which a signal is recorded (FIGS. 1, 2). The M-mode representation is obtained in echographic instruments by a direct recording of the ultrasound signal received along a scanline (FIG. 1).

More recently methods for generating and display M-mode images where the spatial direction is not restricted to be along a scanline have been introduced (FIG. 2). These methods, that permit to create a M-mode image from a sequence of echographic images, are described in U.S. Pat. No. 5,515,856 (1996 Vingmed), also RE37,088 "Method for generating anatomical M-mode displays";

U.S. Pat. No. 5,820,561 (1996 Vingmed), "Analysis and measurement of temporal tissue velocity information";

U.S. Pat. No. 6,589,175 (Philips), "Real-time arbitrary mmode for ultrasonic imaging system".

More recently, the use of M-mode images for the quantitative analysis of time-varying quantities on a sequence of images has been introduced in WO 03 071950 (AMID SRL) also PCT/IT02/00114 filed on Feb. 27, 2002, "M-tracking for space-time imaging".

A further application based on the combined sequence of quantitative analysis of M-mode images has been introduced in EP 03 42 5639 (Esaote SPA, AMID SRL) filed on Sep. 30, 2003 entitled "A method of tracking position and velocity of objects' borders in two or three dimensional digital images, particularly in echographic images" in which application the method of creating the M-mode image from line or curve draw on one frame of a sequence of images, has been further improved by using a line or curve with a thickness that is larger than a single pixel and taking the average signal value across such thickness. This improvement allows to generate M-mode images that are less noisy than those obtained from regular M-mode.

The M-mode representation is widely used in echocardiography for the assessment of mechanical timings, like contraction of cardiac chamber, valvular opening etc. This representation is very important in diagnosis and indeed the mechanical timing is employed in conjunction with timing of electrical events, electrocardiogram (ECG).

Other parameters which describes, are generated or related to the time varying event in the target body can be obtained by measuring different physical or physiological effects by means of probes which reacts to the effects and generate a corresponding time dependent measurement signal generally an electric or electromagnetic signal. The electrocardiogram is an example of such kind of apparatus which furnishes a time dependent electric measurement signal related to the cardiac activity.

In most field, the principal graphic display of dynamic quantities i.e. of the time dependent measurement signal or of a signal obtained by further treating the measurement signal for the extraction of the relevant part of information desired, is the presentation in the form of a XY graph of a function $y=f(t)$ where t is the time, or the abscissa, typically the horizontal axis, y is the ordinate, and f is a generic functional relationship that can be mathematically known (explicitly or implicitly), be the result of a computation or of measurements. Such a representation shows the evolution of one or more quantities in time (FIG. 3).

It is known to associate measurements of a target body made by means of ultrasound imaging methods with measurements of one or more of other relevant parameters by means of probes furnishing time dependent signals in the meaning defined above.

Nevertheless this time dependent measurement signals are used basically for triggering the ecographic image acquisition and are displayed in a separate manner.

Present known methods do not offer a way to reveal and explicit show dynamic relations between the different time dependent measurements signals and the information of the ecographic images.

The present invention aims to improve the present measurement methods by allowing in a simple, rapid and non expensive way to reveal and recognize immediately dynamic relationships between the different measurements signals and the ecographic images.

The present invention achieves the above mentioned aims by means of a measurement method of time varying events in a target body, comprising the steps of:

a) Providing one or more time dependent measurements signals of one or more parameters of the time varying events in the target body by means of one or more measurement devices or probes;

b) Providing one or more ecographic M-mode (Motion mode) image data where the space direction is along one or more scan-lines or curves;

c) defining a time interval within which the measurement signals has to be displayed and/or evaluated;

d) defining a time instant of begin of the said time interval having a univoquely relation to one or more time varying events;

e) generating a bi-dimensional graph of the function corresponding to each said time dependent measurement signal one direction of the said bi-dimensional graph being the time axis;

f) generating one or more bi-dimensional M-mode images, the time axis being chosen as having the same direction of the graph of the function corresponding to the said time dependent measurement signals;

g) determining in each graph of the function corresponding to each said time dependent measurement signal and in the M-mode images the time instant of begin of the said time interval having a univoquely relation to one or more time varying events;

h) rescaling the time scale of each graph of the function corresponding to each said time dependent measurement signal and of the M-mode images to a unique and identical time scale in which the said defined time interval has an equal length along the time axis;

i) displaying the graph of the function corresponding to one or more of the said time dependent measurement signal on a background formed by one or more of the M-mode images by aligning the said time instant of begin of the said time interval in a coincident position.

Advantageously the colours or shades of the graph of the function corresponding to one or more of the said time dependent measurement signal and of the M-mode images are modified in order to be different form each other.

In order to harmonize the dimensions of the said graphs and of the said M-mode images, the graphs of the function corresponding to one or more of the said time dependent measurement signal and/or the M-mode images are extended or reduced in a direction orthogonal to the time axis When at least two M-mode images are provided these can be displayed one adjacent to the other in a direction orthogonal to the time axis. Similarly when at least two graphs representing the function corresponding to the time dependent measurement signal of two different parameters are provided these can be displayed shifted one with respect to the other in a direction orthogonal to the time axis.

At least part or all of the ecographic data for generating the M-mode images and of the time dependent measurement signals are measured or acquired during the same time.

At least part or all of the ecographic data for generating the M-mode images and of the time dependent measurement signals are measured or acquired during different times.

According to a further feature the ecographic data for generating one or more of the M-mode images may be directly acquired by a repeated firing of ultrasound beams and by receiving of the reflected ultrasound beams along a scan line at least for a time period corresponding to the said defined time period.

It is also possible that the ecographic data for generating one or more of the M-mode images is reconstructed form a time sequence of two dimensional or three dimensional ecographic image data by defining at least a scan line and reconstructing the image data along the said scan-line from the intersection of the said scan-line with the two or three dimensional ecographic image data as disclosed in the above cited references.

The scan lines of at least one of the M-mode images may be chosen having a rectilinear shape or an arbitrary curved shape.

Further improvements and features of the present invention are subject of the dependent claims.

The above innovative approach allows to combined the display of different quantities and the immediate comparison of their dynamics. It has a formidable impact for the improvement of the diagnostic capability in cardiology.

The measurement method according to the present invention can be directed to target bodies being a biologic body or an anatomical district or a part of an anatomical district of a biological being and particularly to the cardiac district and tissues.

In this case the time dependent measurement signal is an electrocardiogram (ECG) signal and the at least one M-mode image is an echocardiographic image.

In a particularly advantageous embodiment the scan line along which the echocardiographic image is taken is chosen so to cross one or more ventricular tissue elements particularly the annulus and the anterior mitral valve leaflet and/or the ventricle wall.

Further time dependent signals can be measured and displayed consisting for example in the time profile of the left ventricular volume and/or the strain of the lateral wall and/or the strain of the intraventricular septum.

The invention relates furthermore to a method for displaying measurement data of different parameters of a target in which time dependent events occur, which measurement data consist in at least an ecographic M-mode image and in at least a two dimensional graph representing a time dependent measurement signal, the said method comprising the steps of displaying the two dimensional graph laid over the M-mode image as a background.

More particularly the said method comprises the following steps:

a) defining a time interval within which the measurement data has to be displayed and/or evaluated;

b) defining a time instant of begin of the said time interval having a univoquely relation to one or more time varying events;

c) generating a bi-dimensional graph of the function corresponding to the said at least one time dependent measurement signal, one direction of the said bi-dimensional graph being the time axis;

d) generating a bi-dimensional M-mode image the time axis being chosen as having the same direction of the graph of the function corresponding to the said time dependent measurement signal;

e) determining in each graph of the function corresponding to the said at least one time dependent measurement signal and in the at least one M-mode image the time instant of begin of the said time interval having a univoquely relation to one or more time varying events;

f) rescaling the time scale of the graph of the function corresponding to the said at least one time dependent measurement signal and of the at least M-mode images to a unique and identical time scale in which the said defined time interval has an equal length along the time axis;

i) displaying the graph of the function corresponding to the said at least one time dependent measurement signal on a background formed by the said at least one M-mode images by aligning the said time instant of begin of the said time interval in a coincident position.

Further details or improvement of the said method are disclosed in the dependent claims.

The features and the advantages of the present invention will be disclosed in greater detail in the following description of some examples and by the annexed drawings.

BRIEF SUMMARY OF THE INVENTION

A measurement method of time varying events in a target body according to one embodiment of the present invention comprises the steps of a) providing one or more time dependent measurements signals of one or more parameters of the time varying events in the target body by means of one or more measurement devices or probes; b) providing one or more ecographic M-mode (Motion mode) image data whose spatial direction is along one or more scan-lines or curves; c) defining a time interval within which the measurement signals has to be displayed and/or evaluated; d) defining a time instant of begin of the said time interval having a univoquely relation to one or more time varying events; e) generating a bi-dimensional graph of the function corresponding to each said time dependent measurement signal one direction of the said bi-dimensional graph being the time axis; f) generating one or more bi-dimensional M-mode images, the time axis being chosen as having the same direction of the graph of the function corresponding to the said time dependent measurement signals; g) determining in each graph of the function corresponding to each said time dependent measurement signal and in the M-mode images the time instant of begin of the said time interval having a univoquely relation to one or more time varying events; h) rescaling the time scale of each graph of the function corresponding to each said time dependent measurement signal and of the M-mode images to a unique and identical time scale in which the said defined time interval has an equal length along the time axis; and i) displaying the graph of the function corresponding to one or more of the said time dependent measurement signal on a background formed by one or more of the M-mode images by aligning the said time instant of begin of the said time interval in a coincident position.

One object of the present invention is to provide an improved measurement method of time varying events in a target body.

Related objects and advantages of the present invention will be apparent from the following description.

DETAILED DESCRIPTION OF THE INVENTION

Figure 1:
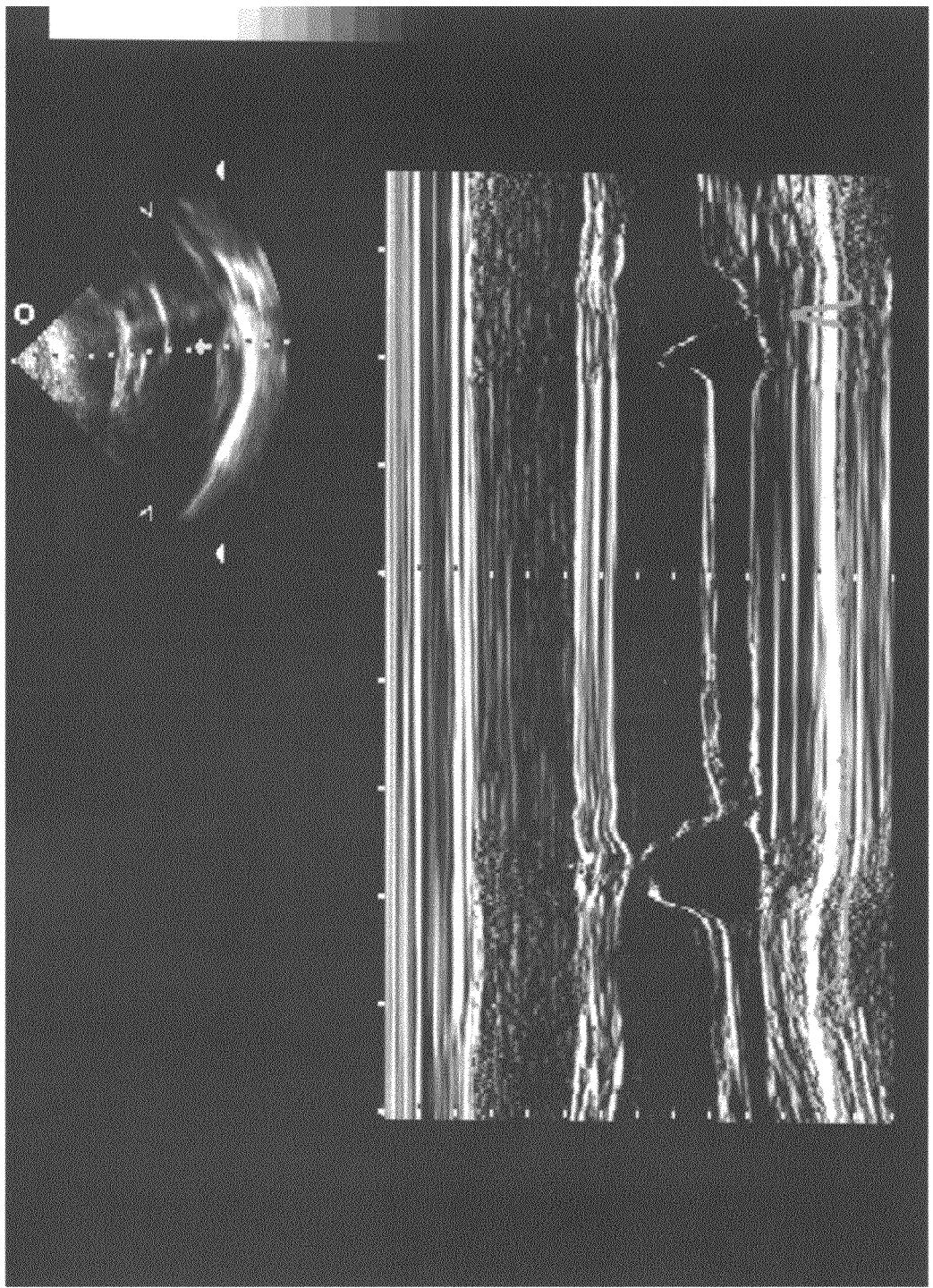
FIG. 1 illustrates a space-time representation, or M-mode image, as recorded directly from echocardiographic equipment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention is described by means of a specific application to the field of diagnostics and particularly to the field of cardiology. Nevertheless this example has not to be considered as limiting the teaching of the present invention to such fields and the scope of protection to the said particular application disclosed as it is clear that the skilled person can adapt the method to different kinds of fields and/or targets without having to carry out other actions that applying the normal skills.

Figure 2:
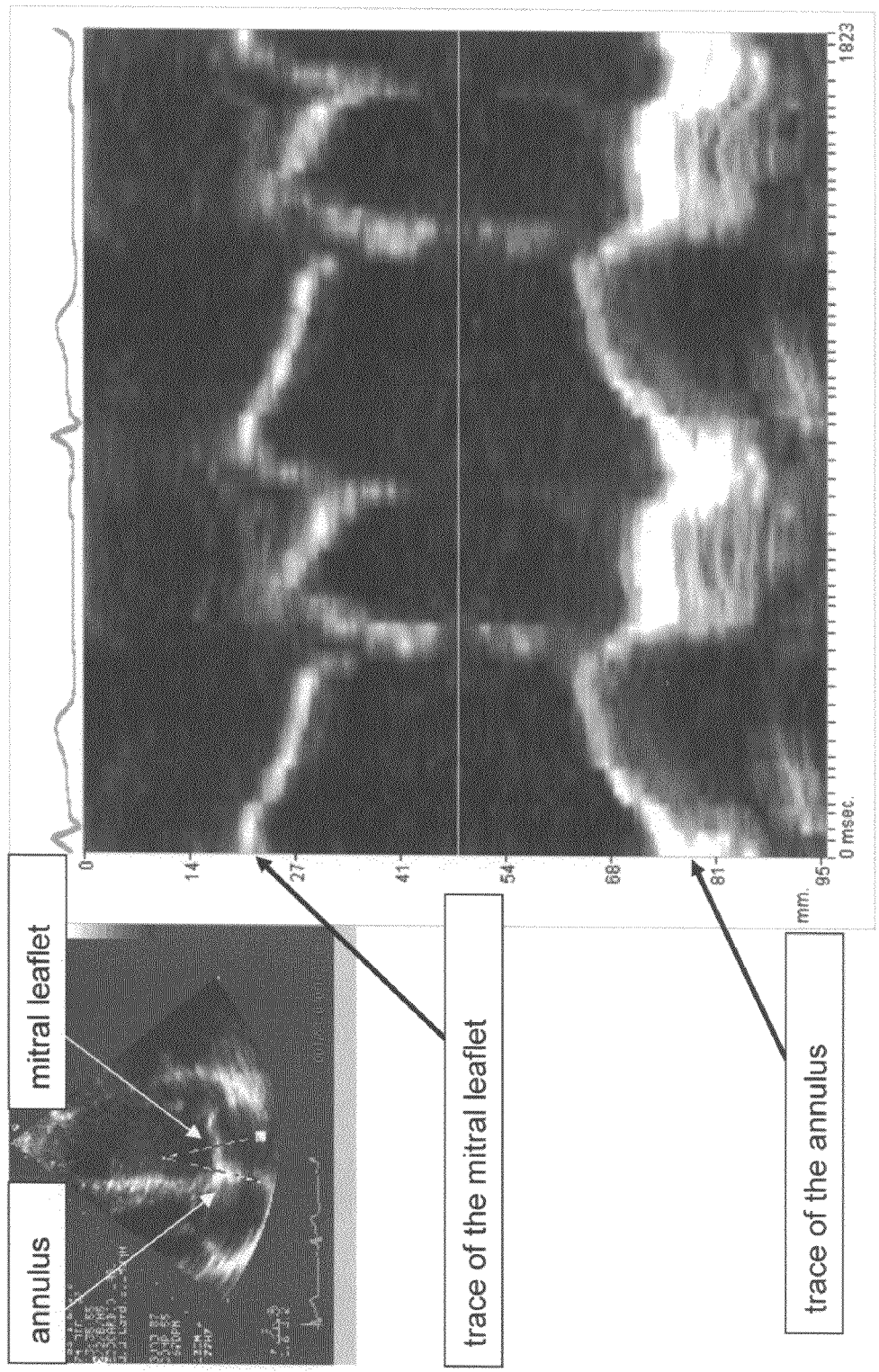
FIG. 2 illustrate a space-time representation, or M-mode image, as reconstructed from a sequence of echocardiographic images.
Figure 3:
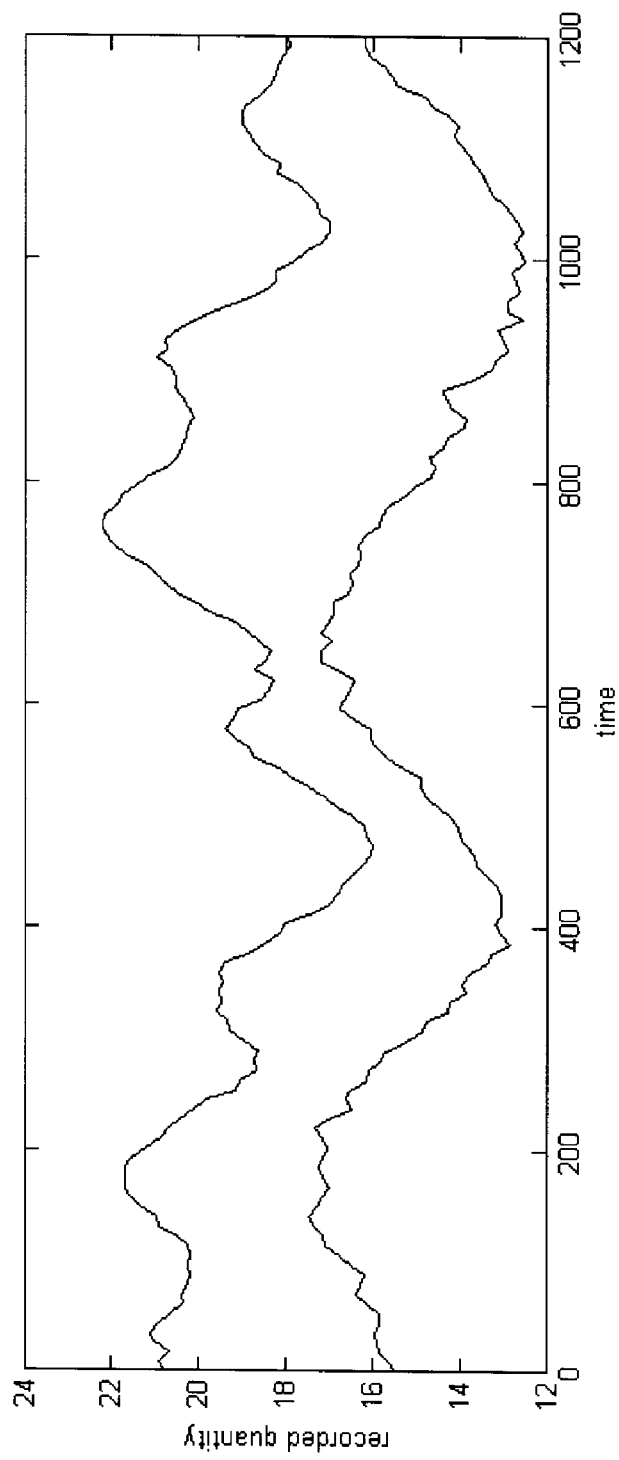
FIG. 3 illustrate the time evolution of recorded quantities shown in a XY representation.

The core of the present invention consists in the following:

Consider that we have built one M-mode image, and that we have the data to be displayed on a XY graph by one or more functions $y=f(t)$ as illustrated in FIG. 3 and which functions refer to the time profile of quantities that correspond to the time interval of a image acquisition. As illustrated by FIGS. 1 and 2 such image can be a directly measured M-mode image, or a sequence of 2D images, or of 3D volumetric datasets. These techniques for generating M-mode images are known and disclosed for example in U.S. Pat. No. 5,515,856, issued May 14, 1996 to Olstad et al.; U.S. Pat. No. 5,820,561, issued Oct. 13, 1998 to Olstad et al.; and U.S. Pat. No. 6,589,175, issued Jul. 8, 2003 issued to Prater et al. Such functions $y=f(t)$ have been measured or calculated either independently from such image sequence or evaluated from the quantification of data contained in the image sequence.

More particularly FIG. 1 shows the space-time representation, or M-mode image, as recorded directly from a echocardiographic equipment. Time is the horizontal axis, space is along a line in crossing the cardiac tissue. The space line position is shown on the top-right inset. Timing of contraction and expansion can be read in this representation.

FIG. 2 shows the space-time representation, or M-mode image, as reconstructed from a sequence of echocardiographic images. Time is the horizontal axis, space is along a curve crossing the cardiac tissue in two regions. The spatial curve position, shown on the left panel, is constructed such that the space curve crosses two left ventricular tissue elements, the annulus and the anterior mitral valve leaflet. A curve thickness of 5 points (2 per each side) has been used to obtain an improved M-mode representation.

As illustrated in FIG. 2, further to obtaining the M-mode image data from direct ultrasound signal along a scanline, or along one line or curve drawn over one or more frames of an image sequence, of 2D images or 3D datasets, as a further improvement for the quality of the M-mode image, the line or curve can have a thickness larger than that of a single pixel and the signal is built by extracting the average value across such a thickness. This technique is disclosed with greater detail in EP 03 42 5639 (Esaote SPA, AMID SRL) filed on Sep. 30, 2003.

Once the M-mode image has been reconstructed or generated, the M-mode image is taken to be the background over which the XY graph is plotted. An example of such XY graphs of time dependent functions $y=f(t)$ is illustrated in FIG. 3. To achieve this the horizontal, time direction, is adapted such that the size of the M-mode is the same of that of the XY graph along the same time limits. The vertical, space direction, size of the M-mode can be expanded or shrunk, or the image cropped, such that it properly fits in the size of the XY graph along the desired limits. In this way the y=f(t) curves, in a XY display, is plotted on a background made of the M-mode image.

The functions y=f(t) can be obtained by direct measurements of parameters by means of probes which are sensible to such parameters or can be obtained by further elaborating one or more time dependent measurement signals in order to extract from them a part of the recorded information which is considered relevant. As this is the case for the functions representing the time dependent evolution of the left ventricular volume in FIG. 4 and the time dependent evolution of the myocardial strain (tissue shortening/elongation) on two regions of the left ventricle wall, namely the intraventricular septum (IVS, light gray) and the lateral wall (LW, dark gray) in FIG. 5.

This quantities can be obtained for example by a method disclosed in EP 1 522 875 and/or EP 1 520 517 (Esaote SPA, AMID SRL) by using also the data collected by means of M-mode or B-mode ultrasound imaging.

For further improvement of the quality and readability of the resulting image, the colors of the M-mode image can be changed from the original ones, if any, by changing color palette or by adjustments, like contrast, brightness, gamma, equalization, or any linear or nonlinear filtering procedure. Similarly, the XY curves colors can be changed from the original, if any, or modified in drawing specification.

Figure 4:
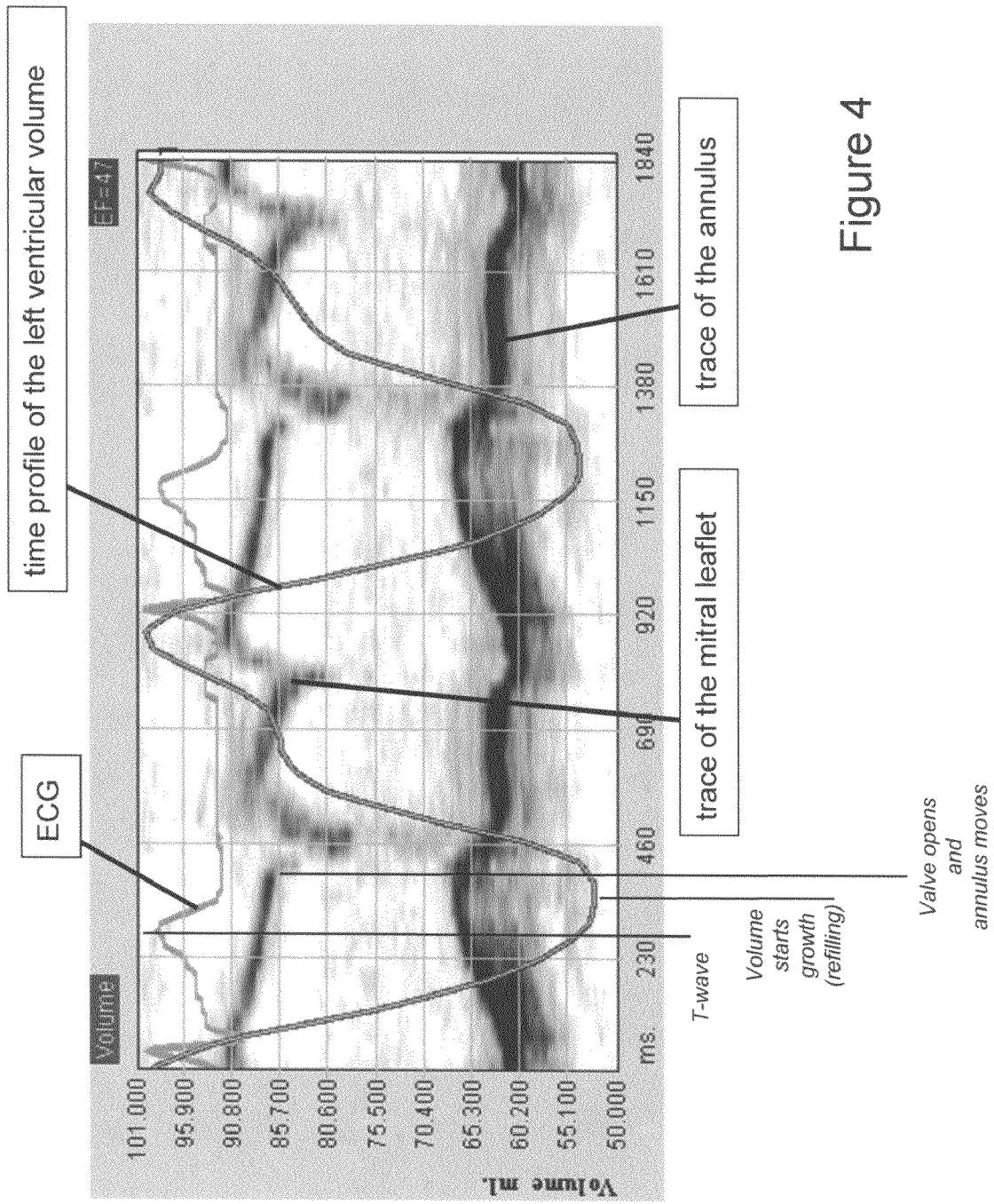
FIG. 4 shows an XY display of the evolution of the left ventricular volume, with ECG, drawn on a background of a space-time representation, or M-mode image, constructed such that the space curve crosses two left ventricular tissue elements, the annulus and the anterior mitral valve leaflet. The M-mode image is that shown in FIG. 2, M-mode colors are modified from those of the originals image sequence to enhance readability.
Figure 5:
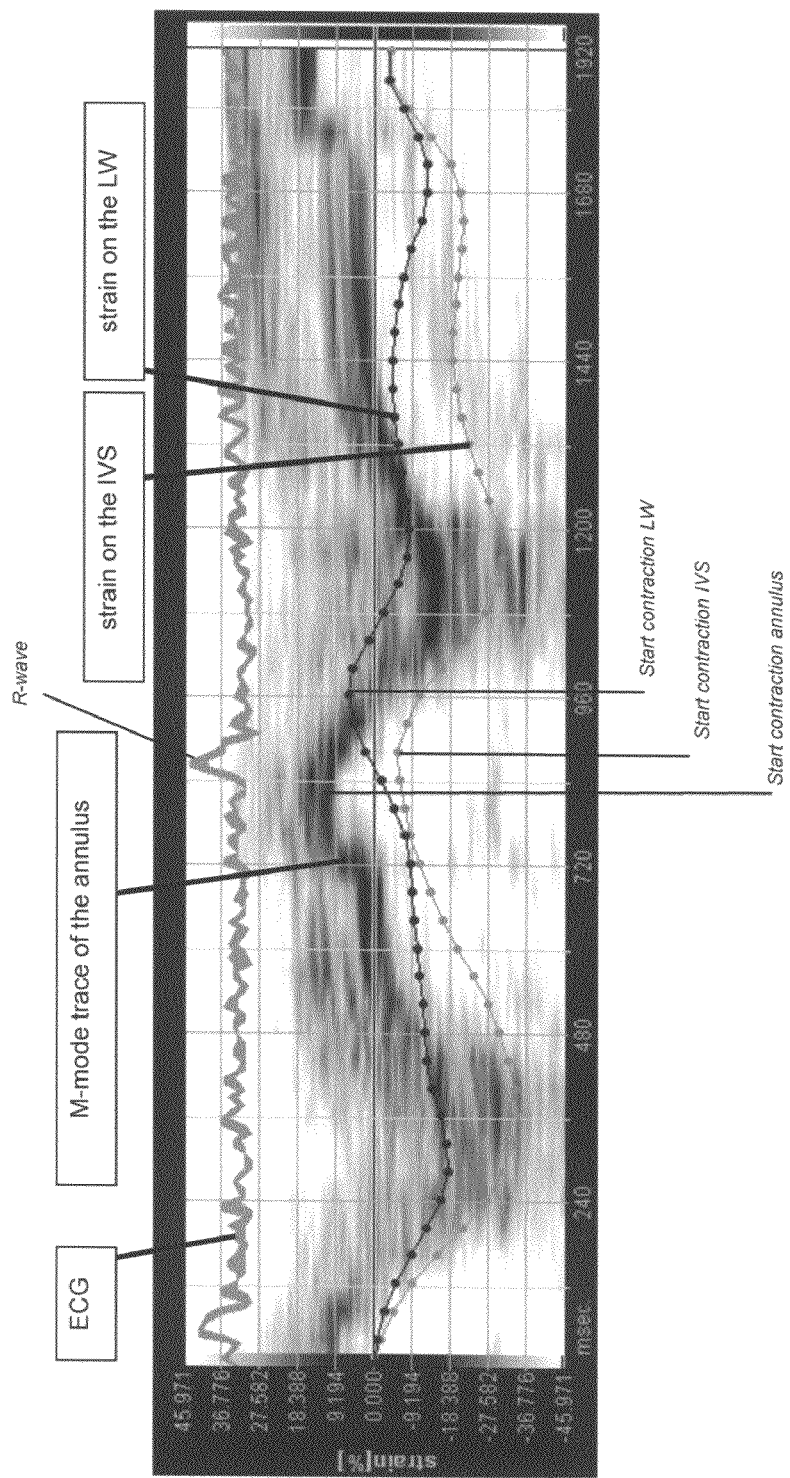
FIG. 5 shows an XY display of the evolution of the myocardial strain (tissue shortening/elongation) on two regions of the left ventricle wall: the intraventricular septum (IVS, light gray) and the lateral wall (LW, dark gray). The graph is drawn on a background M-mode of the annulus whose motion gives an evaluation of the global ventricular contraction. The image is extracted from a patient with suspect synchronization pathology and is employed to verify this lack of synchronization and to evaluate which wall, if any, presents an incorrect activation of contractility.

The result is a graphic XY display, on a background M-mode, two example are shown in FIGS. 4, 5.

The example of FIG. 4 shows how the method according to the present invention permits to evaluate quantities that could not be accessible otherwise. In this case the time delays between the electrical start of diastole, the mechanical start, and the valvular opening, that are known to be related to the physiological function of the left ventricle are evaluated. The evaluation of proper timings and the delay between contractile or relaxation events in different regions of the left ventricle is known to be of primary importance in the diagnosis of cardiac synchronicity and subsequent resynchronization therapy, like implant of pace-maker.

FIG. 4 illustrates the XY display of the evolution of the left ventricular volume, with ECG, drawn on a background of a space-time representation, or M-mode image, constructed such that the space curve crosses two left ventricular tissue elements, the annulus and the anterior mitral valve leaflet. The M-mode image is that shown in FIG. 2, M-mode colors are modified from those of the originals image sequence to enhance readability.

The analysis of timings shows that the beginning of diastole as an electrical event and given by the T-wave of the ECG, precedes the mechanical beginning of diastole that is represented by the beginning of volume growth. Moreover, the volume begins to grow a little before the mitral valve opens. This little period is that necessary for the ventricular pressure to decrease enough and allow valvular opening. The extension of this little period is known to be highly variable in pathologic conditions. This representation allows its evaluation and use in the diagnostic process. A similar argument can be employed about timings of systole.

The example of FIG. 5 shows how the presence of a background M-mode has permitted to indicate the correct region requiring therapy, a wrong evaluation of this could worsen the cardiac function after the implant of a pace-maker.

FIG. 5 shows the XY display of the evolution of the myocardial strain (tissue shortening/elongation) on two regions of the left ventricle wall: the intraventricular septum (IVS, light gray) and the lateral wall (LW, dark gray). The graph is drawn on a background M-mode of the annulus whose motion gives an evaluation of the global ventricular contraction.

The image is extracted from a patient with suspect synchronization pathology and is employed to verify this lack of synchronization and to evaluate which wall, if any, presents an incorrect activation of contractility.

Contraction is normally expected to begin, for electrical activation, after the R-wave of the ECG signal. However the ECG trace could be not a proper timing indicator in patient with a pathologic electrical activity, like this could be the case.

The contraction on the intraventricular septum (IVS) and on the lateral wall (LW) appear not to be in phase as they should under healthy conditions. Contraction begins later on the LW than on the IVS. The former contracts after the R-wave possibly indicating that the LW is properly activated while the IVS contraction is anticipated.

The background M-mode of the annulus shows, instead, that the overall, long axis, ventricular contraction is approximately in phase with the IVS, and the LW has a delayed contraction. The support of a background M-mode suggests, in this case, that the myocardial tissue of the LW is the proper region to correct in a resynchronization therapy (pace-maker implant).

As it appears clearly from the above the innovative approach according to the present invention allows to combine the display of different quantities and the immediate comparison of their dynamics. It has a formidable impact for the improvement of revealing the exact conditions of a target body in which time varying events occur and in the case of the present non limiting example in particular field of the diagnostic in cardiology.

As already cited the data for drawing the XY graph of the time dependent evolution of the ventricular volume and of the time dependent evolution of the strain of the intraventricular septum (IVS, light gray) and of the lateral wall (LW, dark gray) can be obtained by using a known method like ones based on Tissue Doppler echocardiography as disclosed in U.S. Pat. No. 6,352,507, issued Mar. 5, 2003 to Torp, et al., and/or U.S. Pat. No. 6,537,221, issued Mar. 25, 2003 to Criton et al., and/or as reported in the literature (Urheim et al. Circulation 2000, 102:1158-1164; D'hooge et al., Eur J Echocardiography 2000, 1:154-170), or another method based on processing of B-mode echographic imaging disclosed in EP 1 522 875 and/or EP 1 520 517 (Esaote SPA, AMID SRL).

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A method for displaying measurement data of different parameters of a biological target body in which time dependent events occur, the method comprising the following steps:
 a) defining a time interval within which the measurement data has to be displayed and/or evaluated;
 b) defining a time instant of begin of the time interval time varying event;
 c) generating a bi-dimensional graph of a function corresponding to at least one time dependent measurement signal, one direction of the bi-dimensional graph being a time axis;
 d) generating a M-mode image from echographic data recorded from echocardiographic equipment, the M-mode image having the time axis being chosen as having the same direction of the bi-dimensional graph of the function corresponding to the said time dependent measurement signal, the echographic data for generating the M-mode image having been directly acquired by a repeated firing of ultrasound beams and by receiving of the reflected ultrasound beams along a scan line at least for a time period corresponding to said defined time period, the scan line passes through an anatomical district comprising a bodily organ, the bodily organ has at least two moving parts which have a synchronized movement, the scan line passes through all of the synchronized moving parts;

e) determining in each bi-dimensional graph of the function corresponding to the said at least one time dependent measurement signal and in the M-mode image the time instant of begin of the said time interval;

f) resealing the time scale of the bi-dimensional graph of the function corresponding to the said at least one time dependent measurement signal and of the M-mode image to a unique and identical time scale in which the said defined time interval has an equal length along the time axis; and g) displaying the bi-dimensional graph of the function corresponding to the said at least one time dependent measurement signal, the bi-dimensional graph is directly overlaid on a background formed by the M-mode image by aligning the said time instant of begin of the said time interval in a coincident position, wherein the biological target body is a heart and time dependent measurement signal is an electrocardiographic (ECG) signal.

2. A method according to claim 1, characterized in that the colours or shades of the graph of the function corresponding to the said at least one time dependent measurement signal and/or of the M-mode image are modified in order to be different form each other.

3. A method according to claim 2, characterized in that the graph of the function corresponding to the said at least one time dependent measurement signal and/or of the M-mode image are extended or reduced in a direction orthogonal to the time axis.

4. A method according to claim 3, characterized in that at least two M-mode images are provided which are displayed one adjacent to the other in a direction orthogonal to the time axis.

5. A method according to claim 4, characterized in that at least two graphs representing the function corresponding to the time dependent measurement signal of two different parameters are provided which are displayed shifted one with respect to the other in a direction orthogonal to the time axis.

6. A method according to claim 1, characterized in that a portion of the function represented by the bi-dimensional graph is an elaboration of the time dependent measurement signal.

7. A method according to claim 1, characterized in that at least part or all of the echographic data for generating the M-mode image and of the time dependent measurement signals are measured or acquired during the same time.

8. A method according to claim 1, characterized in that at least part or all of the echographic data for generating the M-mode image and of the time dependent measurement signals are measured or acquired during different times.

9. A method according to claim 1, characterized in that the echographic data for generating one or more M-mode images has been reconstructed from a time sequence of two dimensional or three dimensional echographic image data by defining at least a scan line and reconstructing the image data along the said scan-line from the intersection of the said scan-line with the two or three dimensional echographic image data.

10. A method according to claim 1, characterized in that the scan line of at least one of the M-mode images is rectilinear or an arbitrary shaped curved line.

11. A method according to claim 10, characterized in that the target body is a biologic body or an anatomical district or a part of an anatomical district of a biological being.

12. A method according to claim 1, characterized in that at least one M-mode image is an echocardiographic image.

13. A method according to claim 12, characterized in that the scan line along which the echocardiographic image is taken so to cross one or more ventricular tissue elements particularly the annulus and/or a valvular leaftlet and/or the ventricle wall.

14. A method according to claim 13, characterized in that one of the time dependent measurement signal is the time profile of one heart chamber volume.

15. A method according to claim 14, wherein one of the time dependent measurement signal is the strain and/or the strainrate of a region of the tissue.

16. A method according to claim 15 wherein one of the time dependent measurement signal is a property, one component and/or the module and or the angle, of the velocity vector and/or the displacement vector of a region of the tissue.

17. A method according to claim 1, characterized in that it is a method for revealing diagnostic data.

18. A method according to claim 1, characterized in that it is a method for revealing relationship of diagnostic data in cardiology.

19. A method according to claim 1, characterized in that it is a method for graphic display and comparison of the time dependent dynamics of different diagnostic cardiologic parameters.

20. A method according to claim 1, characterized in that it is a cardiologic diagnostic method.

21. A method for displaying measurement data of different parameters of a biological target body in which time dependent events occur, the method comprising the following steps:

a) defining a time interval within which the measurement data has to be displayed and/or evaluated;

b) defining a time instant of begin of the time interval as a start time of a time varying event;

c) generating a bi-dimensional graph of a function corresponding to at least one time dependent measurement signal, one direction of the bi-dimensional graph being a time axis;

d) generating a M-mode image from data recorded from echocardiographic equipment, the M-mode image having the time axis being chosen as having the same direction of the bi-dimensional graph of the function corresponding to the said time dependent measurement signal, the echographic data for generating the M-mode image having been directly acquired by a repeated firing of ultrasound beams and by receiving of the reflected ultrasound beams along a scan line at least for a time period corresponding to said defined time period, the scan line passes through an anatomical district comprising a bodily organ, the bodily organ has at least two moving parts which have a synchronized movement, the scan line passes through all of the synchronized moving parts;

e) determining in each bi-dimensional graph of the function corresponding to the said at least one time dependent measurement signal and in the M-mode image the time instant of begin of the said time interval;

f) rescaling the time scale of the bi-dimensional graph of the function corresponding to the said at least one time dependent measurement signal and of the M-mode image to a unique and identical time scale in which the said defined time interval has an equal length along the time axis; and g) displaying the bi-dimensional graph of the function corresponding to the said at least one time dependent measurement signal, the bi-dimensional graph is directly overlaid on a background formed by the M-mode image by aligning the said time instant of begin of the said time interval in a coincident position, wherein the biological target body is a heart and the time dependent measurement signal is the time profile of one heart chamber volume.

22. A method for displaying measurement data of different parameters of a biological target body in which time dependent events occur, the method comprising the following steps:

a) defining a time interval within which the measurement data has to be displayed and/or evaluated;

b) defining a time instant of begin of the time interval as a start time of a time varying event;

c) generating a bi-dimensional graph of a function corresponding to at least one time dependent measurement signal, one direction of the bi-dimensional graph being a time axis;

d) generating a M-mode image from data recorded from echocardiographic equipment, the M-mode image having the time axis being chosen as having the same direction of the bi-dimensional graph of the function corresponding to the said time dependent measurement signal, the echographic data for generating the M-mode image having been directly acquired by a repeated firing of ultrasound beams and by receiving of the reflected ultrasound beams along a scan line at least for a time period corresponding to said defined time period, the scan line passes through an anatomical district comprising a bodily organ, the bodily organ has at least two moving parts which have a synchronized movement, the scan line passes through all of the synchronized moving parts;

e) determining in each bi-dimensional graph of the function corresponding to the said at least one time dependent measurement signal and in the M-mode image the time instant of begin of the said time interval;

f) resealing the time scale of the bi-dimensional graph of the function corresponding to the said at least one time dependent measurement signal and of the M-mode image to a unique and identical time scale in which the said defined time interval has an equal length along the time axis; and g) displaying the bi-dimensional graph of the function corresponding to the said at least one time dependent measurement signal, the bi-dimensional graph is directly overlaid on a background formed by the M-mode image by aligning the said time instant of begin of the said time interval in a coincident position, wherein the biological target body is cardiac tissue and the time dependent measurement signal is the strain and/or the strainrate of a region of the cardiac tissue.

23. A method for displaying measurement data of different parameters of a biological target body in which time dependent events occur, the method comprising the following steps:

a) defining a time interval within which the measurement data has to be displayed and/or evaluated;

b) defining a time instant of begin of the time interval as a start time of a time varying event;

c) generating a bi-dimensional graph of a function corresponding to at least one time dependent measurement signal, one direction of the bi-dimensional graph being a time axis;

d) generating a M-mode image from data recorded from echocardiographic equipment, the M-mode image having the time axis being chosen as having the same direction of the bi-dimensional graph of the function corresponding to the said time dependent measurement signal, the echographic data for generating the M-mode image having been directly acquired by a repeated firing of ultrasound beams and by receiving of the reflected ultrasound beams along a scan line at least for a time period corresponding to said defined time period, the scan line passes through an anatomical district comprising a bodily organ, the bodily organ has at least two moving parts which have a synchronized movement, the scan line passes through all of the synchronized moving parts;

e) determining in each bi-dimensional graph of the function corresponding to the said at least one time dependent measurement signal and in the M-mode image the time instant of begin of the said time interval;

f) resealing the time scale of the bi-dimensional graph of the function corresponding to the said at least one time dependent measurement signal and of the M-mode image to a unique and identical time scale in which the said defined time interval has an equal length along the time axis; and g) displaying the bi-dimensional graph of the function corresponding to the said at least one time dependent measurement signal, the bi-dimensional graph is directly overlaid on a background formed by the M-mode image by aligning the said time instant of begin of the said time interval in a coincident position, wherein the biological target body is cardiac tissue and the time dependent measurement signal is a property of the velocity vector and/or the displacement vector of a region of the cardiac tissue.

24. A method for displaying measurement data of different parameters of a biological target body in which time dependent events occur, the method comprising the following steps:

a) defining a time interval within which the measurement data has to be displayed and/or evaluated;

b) defining a time instant of begin of the time interval as a start time of a time varying event;

c) generating a plurality of bi-dimensional graphs based on functions corresponding to a plurality of time dependent measurement signals, one direction of the bi-dimensional graphs being a time axis;

d) generating a M-mode image from data recorded from echocardiographic equipment, the M-mode image having the time axis being chosen as having the same direction of the bi-dimensional graphs of the function corresponding to the time dependent measurement signals, the echographic data for generating the M-mode image has been directly acquired by a repeated firing of ultrasound beams and by receiving of the reflected ultrasound beams along a scan line at least for a time period corresponding to said defined time period, the scan line passes through an anatomical district comprising a bodily organ, the bodily organ has at least two moving parts which have a synchronized movement, the scan line passes through all of the synchronized moving parts;

e) determining in each of the bi-dimensional graphs and in the M-mode image the time instant of begin of the said time interval;

f) resealing the time scale of the bi-dimensional graphs and of the M-mode image to a unique and identical time scale in which the said defined time interval has an equal length along the time axis; and g) displaying the bi-dimensional graphs of the functions corresponding to the time dependent measurement signals, the bi-dimensional graph is directly overlaid on a background formed by the M-mode image by aligning the said time instant of begin of the said time interval in a coincident position, wherein the biological target body is cardiac tissue, wherein the time dependent measurement signals are selected from the group of an electrocardiographic (ECG) signal, a time profile of a heart chamber volume, a time profile of a heart chamber volume, the strain and/or the strainrate of a region of the cardiac tissue, and a property of a velocity vector and/or a displacement vector of a region of the cardiac tissue, and wherein a scan line along which the echocardiographic image is taken is arranged so as to cross at least one ventricular tissue elements.

* * * * *